(12) United States Patent
Demmer et al.

(10) Patent No.: US 10,751,542 B2
(45) Date of Patent: Aug. 25, 2020

(54) POWER MANAGEMENT FOR IMPLANTABLE MEDICAL DEVICE SYSTEMS

(71) Applicant: Medtronic, Inc., Minneapolis, MN (US)

(72) Inventors: Wade M. Demmer, Coon Rapids, MN (US); Yong K. Cho, Excelsior, MN (US); Michael F. Hess, Minneapolis, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 25 days.

(21) Appl. No.: 15/783,573

(22) Filed: Oct. 13, 2017

(65) Prior Publication Data

US 2019/0111271 A1    Apr. 18, 2019

(51) Int. Cl.
| | | |
|---|---|---|
| *A61N 1/378* | (2006.01) | |
| *A61N 1/375* | (2006.01) | |
| *A61N 1/368* | (2006.01) | |
| *A61N 1/372* | (2006.01) | |
| A61N 1/37 | (2006.01) | |
| A61B 5/0402 | (2006.01) | |

(52) U.S. Cl.
CPC ......... *A61N 1/3787* (2013.01); *A61N 1/3684* (2013.01); *A61N 1/3756* (2013.01); *A61N 1/37288* (2013.01); *A61N 1/37512* (2017.08); *A61B 5/0402* (2013.01); *A61N 1/3708* (2013.01); *A61N 1/37518* (2017.08)

(58) Field of Classification Search
CPC .............. A61N 1/3787; A61N 1/37512; A61N 1/3684; A61N 1/3756
See application file for complete search history.

(56) References Cited

U.S. PATENT DOCUMENTS

| | | |
|---|---|---|
| 7,565,195 B1 | 7/2009 | Kroll et al. |
| 7,630,767 B1 | 12/2009 | Poore et al. |
| 7,634,313 B1 | 12/2009 | Kroll et al. |
| 8,457,742 B2 | 6/2013 | Jacobson |
| 8,532,785 B1 | 9/2013 | Crutchfield et al. |
| 8,744,572 B1 | 6/2014 | Greenhut et al. |
| 8,798,745 B2 | 8/2014 | Jacobson |

(Continued)

OTHER PUBLICATIONS (PCT/US2018/053354) PCT Notification of Transmittal of the International Search Report and the Written Opinion of the International Searching Authority, dated Dec. 12, 2018, 12 pages.

*Primary Examiner* — Joseph M Dietrich

(57) ABSTRACT

Techniques for minimizing rate of depletion of a non-rechargeable power source, to extend the operational lifetime of an implantable medical device that includes the non-rechargeable power source, by enforcing operational-mode-specific communication protocols whereby inter-device communication between the implantable medical device and another implantable medical device is such that level of power draw from the non-rechargeable power source by the implantable medical device is less than level of power draw from the rechargeable power source by the another implantable medical device for the implantable medical devices to engage in communication with each other.

20 Claims, 8 Drawing Sheets

(56) References Cited

U.S. PATENT DOCUMENTS

| | | |
|---|---|---|
| 9,072,914 B2 | 7/2015 | Greenhut et al. |
| 9,168,380 B1 | 10/2015 | Greenhut et al. |
| 9,192,774 B2 | 11/2015 | Jacobson |
| 9,844,675 B2 | 12/2017 | Hareland et al. |
| 9,937,352 B2 | 4/2018 | Sheldon et al. |
| 10,286,214 B2 | 5/2019 | Demmer et al. |
| 10,350,416 B2 | 7/2019 | Bonner et al. |
| 10,449,366 B2 | 10/2019 | Splett et al. |
| 2006/0241705 A1 | 10/2006 | Neumann et al. |
| 2014/0330326 A1 | 11/2014 | Thompson-Nauman et al. |
| 2014/0379048 A1* | 12/2014 | Von Arx .............. A61N 1/362 607/60 |
| 2015/0224320 A1 | 8/2015 | Stahmann |
| 2015/0297905 A1 | 10/2015 | Greenhut et al. |
| 2015/0335894 A1 | 11/2015 | Bornzin et al. |
| 2015/0360036 A1 | 12/2015 | Kane et al. |
| 2016/0015287 A1 | 1/2016 | Anderson et al. |
| 2016/0015322 A1 | 1/2016 | Anderson et al. |
| 2016/0015984 A1 | 1/2016 | Demmer et al. |
| 2016/0015985 A1 | 1/2016 | Cho et al. |
| 2016/0067490 A1 | 3/2016 | Carney et al. |
| 2016/0114162 A1 | 4/2016 | Sheldon et al. |
| 2016/0114168 A1 | 4/2016 | Demmer et al. |
| 2016/0114169 A1 | 4/2016 | Sheldon et al. |
| 2016/0121127 A1 | 5/2016 | Klimovitch et al. |
| 2016/0121128 A1 | 5/2016 | Fishier et al. |
| 2016/0144190 A1 | 5/2016 | Cao et al. |
| 2016/0144191 A1 | 5/2016 | Sheldon et al. |
| 2017/0049325 A1 | 2/2017 | Schmidt et al. |
| 2017/0105635 A1 | 4/2017 | Cho et al. |
| 2017/0173346 A1 | 6/2017 | Kane et al. |

* cited by examiner

400

POWER MANAGEMENT FOR IMPLANTABLE MEDICAL DEVICE SYSTEMS

TECHNICAL FIELD

The present disclosure is directed to implantable medical devices, and in particular to a system that includes at least one implantable medical device that is rechargeable and at least one implantable medical device that is non-rechargeable.

BACKGROUND

A leadless pacing device is an example of an implantable medical device, and may confer advantages over a conventional pacing device as omission of leads may translate into fewer complications and thus improve patient outcomes. However, many significant technical challenges exist when a leadless pacing device is introduced in a system as a concomitant device. For example, communication between medical devices may be desired to coordinate therapy and/or sensing functions, such as to enable multi-chamber pacing modes. However, such communication may consume the power resources of a leadless pacing device.

SUMMARY

Many significant technical challenges exist when an implantable medical device is introduced in a system as a concomitant device with another implantable medical device. The features or aspects of the present disclosure address many of such technical challenges in example implementations in which a first implantable medical device is configured with a rechargeable power source and a second implantable medical device is configured with a non-rechargeable power source. Specifically, it is contemplated that in practice operational-mode-specific communication protocols may be implemented such that, in some examples, inter-device communication between the first implantable medical device and the second implantable medical device is such that level of power draw from the rechargeable power source by the first implantable medical device is greater than level of power draw from the non-rechargeable power source by the second implantable medical device. Such an implementation may, advantageously, minimize rate of depletion of the non-rechargeable power source and thus extend the operational lifetime of the implantable medical device. Although the present disclosure is not so limited, such features or aspects may be implemented or realized according to the following description and claims.

A system comprising: a first implantable leadless pacing device that includes a rechargeable power source housed therein; and a second implantable leadless pacing device that includes a non-rechargeable power source housed therein; wherein the first implantable leadless pacing device and the second implantable leadless pacing device are configured to operate together as a multi-chamber pacing system according to a programmed operational mode, and wherein the first implantable leadless pacing device and the second implantable leadless pacing device are configured to communicate according to a communication protocol that is specific to the programmed operational mode.

An implantable medical device comprising: a power source that is configured as one of a rechargeable power source or a non-rechargeable power source; electrical pacing circuitry that is coupled to the power source and that is configured to deliver cardiac pacing; communication circuitry that is coupled to the power source and configured to establish a communication link with an other implantable medical device that is arranged in a multi-chamber pacing system with the implantable medical device; and processing circuitry that is coupled to the power source, the electrical pacing circuitry and the communication circuitry, wherein the processing circuitry is configured to: determine a state change of the system, and switch between ones of a plurality of different communication protocols for the implantable medical device to operate according to and in which power draw from the power source for inter-device communication with the other implantable medical device is selected according to an operational mode for at least one of the implantable medical device and the implantable medical device to respond to the state change of the system; wherein a power source of the other implantable medical device is configured as the other one of the rechargeable power source or the non-rechargeable power source and each one of the plurality of different communication protocols is defined such that level of power draw from the non-rechargeable power source is less than level of power draw from the rechargeable power source for inter-device communication between the implantable medical device and the other implantable medical device.

A system comprising: a first medical device that is configured to be implanted in a patient and to draw power from a rechargeable battery housed therein for inter-device communication; and a second medical device that is configured to be implanted in the patient and to draw power from a non-rechargeable battery housed therein for inter-device communication, wherein, responsive to a detected state change of the system, the second medical device is further configured to switch to a communication protocol in which power draw from the non-rechargeable battery for inter-device communication with the first medical device is selected according to operational mode programmed to at least one the first and second medical device.

The details of these and other examples of disclosure are set forth in the accompanying drawings and the description below. Other features, objects, and advantages of the disclosure will be apparent from the description and drawings, and from the claims.

DETAILED DESCRIPTION

Figure 1:
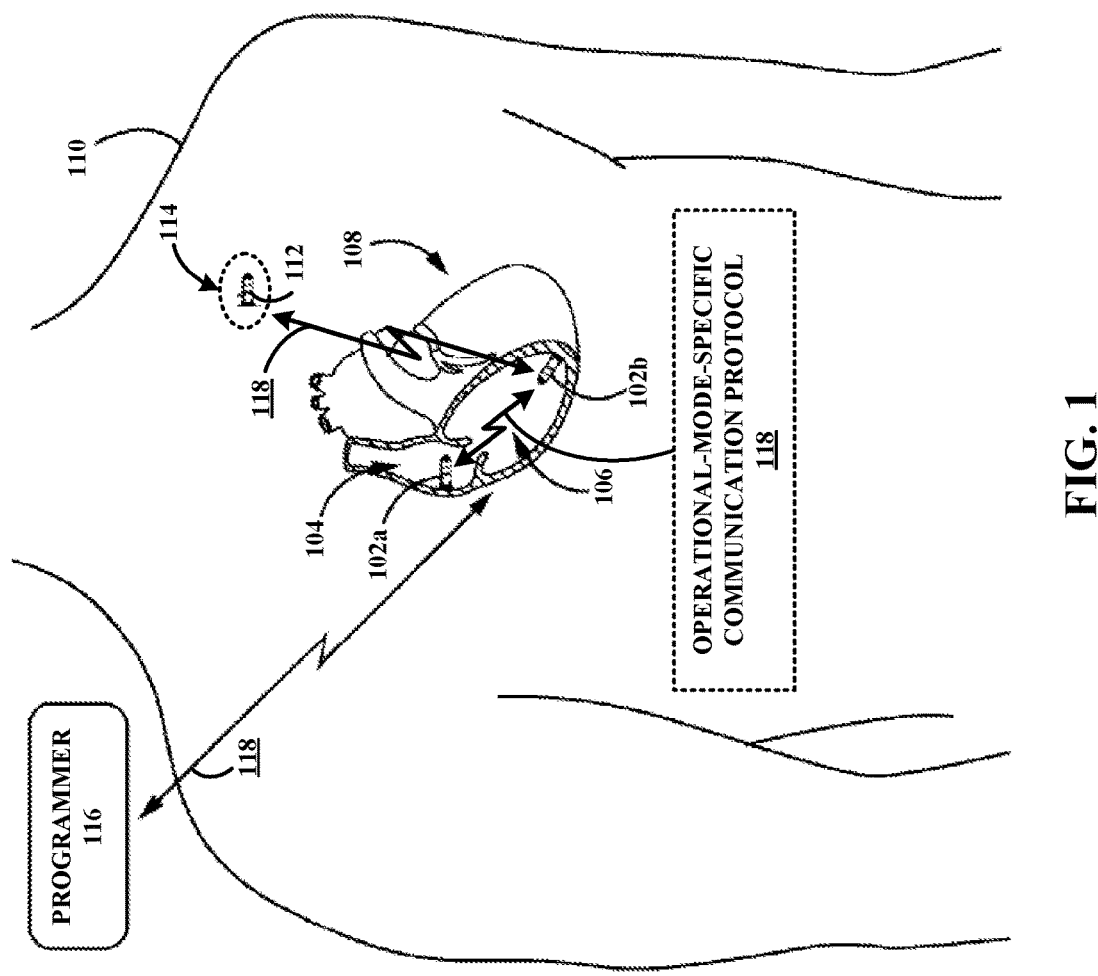
FIG. 1 shows a system that includes at least one rechargeable implantable medical device and at least one non-rechargeable implantable medical device according to the disclosure.

FIG. 1 shows a system 100 that includes at least one rechargeable implantable medical device 102*a* and at least one non-rechargeable implantable medical device 102b according to the disclosure. More specifically, system 100 is an example of an implantable medical device (IMD) system that includes atrial pacing device 102a affixed to tissue in right atrium 104 of heart 108 of patient 110, and that includes ventricular pacing device 102b affixed to tissue in right ventricle 106 of heart 108 of patient 110. In other examples, system 100 may additionally or alternatively include one or more IMDs implanted at other locations in or on the heart. In some examples, system 100 further includes diagnostic device 112 that is implanted subcutaneously and within pocket 114 and that is configured as a dedicated diagnostic monitor. The Reveal LINQ® Insertable Cardiac Monitoring System from Medtronic Public Limited Company, of Fridley, Minn. (operational headquarters) is an example of such a diagnostic device, although other examples are possible.

In the example of FIG. 1, atrial pacing device 102a and ventricular pacing device 102b do not utilize transvenous leads, nor a pocket, but instead are both leadless and wholly implanted within heart 108 of patient 110, and further are configured to implement coordinated atrial and ventricular pacing functions as discussed in detail below in connection with FIGS. 2-8. In general, however, atrial pacing device 102a may be configured to monitor ventricular events and control atrial pacing pulse delivery based on sensed ventricular events (or lack thereof) to promote atrial-ventricular synchrony for patient 110. In this example, atrial pacing device 102a may be considered a "quality-of-life" device and thus atrial pacing device 102a may be configured to include or exhibit a rechargeable power source, or battery, that over the course of its operational lifetime may be recharged to capacity via external means (not shown) by patient 110 or a medical practitioner as required or according to schedule. If the rechargeable power source is depleted such that atrial pacing device 102a is incapable of operating as intended, such as due to human error in failing to (re)charge the same for example, then patient 110 may be symptomatic but such an occurrence may not necessarily be life-threatening.

Ventricular pacing device 102b, on the other hand, may be configured to monitor electrical activity of heart 108 of patient 110 and to control ventricular pacing pulse delivery based on sensed events (or lack thereof). In the present example, ventricular pacing device 102b may be considered a "life-saving" device, as would be understood by one of ordinary skill in the art, and thus ventricular pacing device 102b may be configured to include or exhibit a non-rechargeable power source, or battery, that does not deplete to the extent that ventricular pacing device 102b is incapable of operating as intended due to human error in failing to (re)charge the same. Rather, the non-rechargeable power source (equivalently, ventricular pacing device 102b) may have a finite operational lifetime dictated not only by implementation-specific details, such as type and size of the non-rechargeable power source, as well as patient-condition-specific details, but also by other functions that ventricular pacing device 102b is configured to implement in vivo.

As an example, the non-rechargeable power source may have a finite operational lifetime that is a function of extent by which ventricular pacing device 102b is configured to communicate with one or more of atrial pacing device 102a, diagnostic device 112 and programmer device 116, as illustrated in FIG. 1, for the respective devices to operate together (e.g., communicate) within system 100 as intended. Once the non-rechargeable power source has reached end-of-life (EOL), and preferably prior to EOL, one or both of explant and subsequent implant procedures may be necessary. To reduce the likelihood/frequency of such explant/implant procedures when performed more than once over the lifetime of patient 110, it may be desirable to minimize rate of depletion of the non-rechargeable power source and thus extend the operational lifetime of the implantable medical device. Such a result may, advantageously, minimize or limit the total number of explant/implant procedures patient 110 may be required to endure over time.

Thus, to reduce the rate of non-rechargeable power source depletion in a manner as discussed, it is contemplated that the medical devices of system 100 may collectively implement an operational-mode-specific communication protocol 118 (see FIG. 1) whereby inter-device communication between atrial pacing device 102a and ventricular pacing device 102b (and/or other or different devices in system 100) is such that level of power draw from the non-rechargeable power source is reduced and, in some cases, such that the level of power draw from the rechargeable power source by atrial pacing device 102a is greater than level of power draw from the non-rechargeable power source by ventricular pacing device 102b for atrial pacing device 102a and ventricular pacing device 102b to engage in communication. As discussed below, a particular operational-mode-specific communication protocol, also referred to as "protocol" or "communication protocol" or the like and as used in the context of this disclosure, may represent only one of a plurality of different operational-mode-specific communication protocols, each one associated with one or more corresponding rules that govern an extent by which devices engage in inter-device communication within system 100. Each operational-mode-specific communication protocol may be defined such that level of power draw from a non-rechargeable battery in system 100 is controlled and, in some cases, less than level of power draw from a rechargeable battery for IMD 102 to engage in inter-device communication within system 100.

As an example, and for any one particular operational-mode-specific communication protocol, a ratio of power draw as defined with respect to a sum total power draw for atrial pacing device 102a and ventricular pacing device 102b to engage in communication with each other (i.e., as per a power budget to implement communications) may be quantified as a 2:1 ratio (device 102a:device 102b), or as a 3:1 ratio, or as a 25:1 ratio, or as a 50:1 ratio, or as a 100:1 ratio, or even as a 1000:1 ratio, such that in practice and at all times atrial pacing device 102a is burdened substantially more than ventricular pacing device 102b in terms of power consumption for the purpose of inter-device communication. In this manner, operational lifetime of ventricular pacing device 102b may be extended because load on the non-rechargeable power source may be substantially reduced over time. Put another way, such an implementation as contemplated throughout may minimize rate of depletion of the non-rechargeable power source and thus extend the operational lifetime of ventricular pacing device 102b. An example IMD configured and/or arranged according to such an implementation is illustrated in FIGS. 2-3.

Although primarily described in the context of examples in which both the rechargeable and non-rechargeable IMDs are leadless pacing devices implanted within the heart, the disclosure is not limited to such examples. In some examples, either device may be coupled to leads or implanted outside of the heart. In some examples, the rechargeable IMD may deliver pacing to, e.g., be implanted on or within, the left ventricle, instead of an atrium. Left-ventricular pacing may be considered quality of life therapy, rather than lifesaving, in some examples. In some examples, an IMD that does not deliver pacing may be the rechargeable IMD. For example, diagnostic device 112 or an extravascular (e.g., subcutaneous) implantable cardioverter defibrillator (ICD) may be a rechargeable device that communicates with pacemaker 102b to provide multi-chamber pacing and sensing modes. In general, any two or more IMDs of a system 100, at least one of which is a pacemaker, may communicate to provide multi-chamber pacing and sensing modes, e.g., VDI, VDD, DDI, DDD, VDIR, VDDR, DDIR, DDDR, etc., where one of ordinary skill in the art would understand that the above modes are coded according to the NBG pacemaker code that describes a five letter code (positions I-V, where O=none, A=atrium, V=ventricle, D=dual (A+V), R=rate modulation, I=inhibited, T=triggered) for operation of implantable pacemakers and defibrillators.

Figure 2:
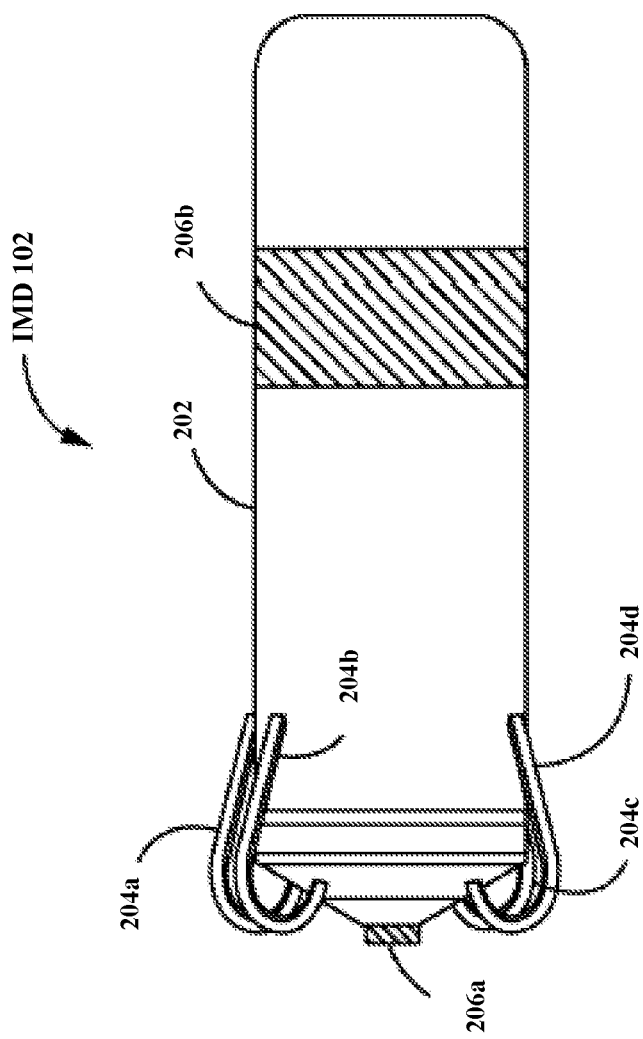
FIG. 2 shows an implantable medical device in first detail according to the disclosure.
Figure 3:
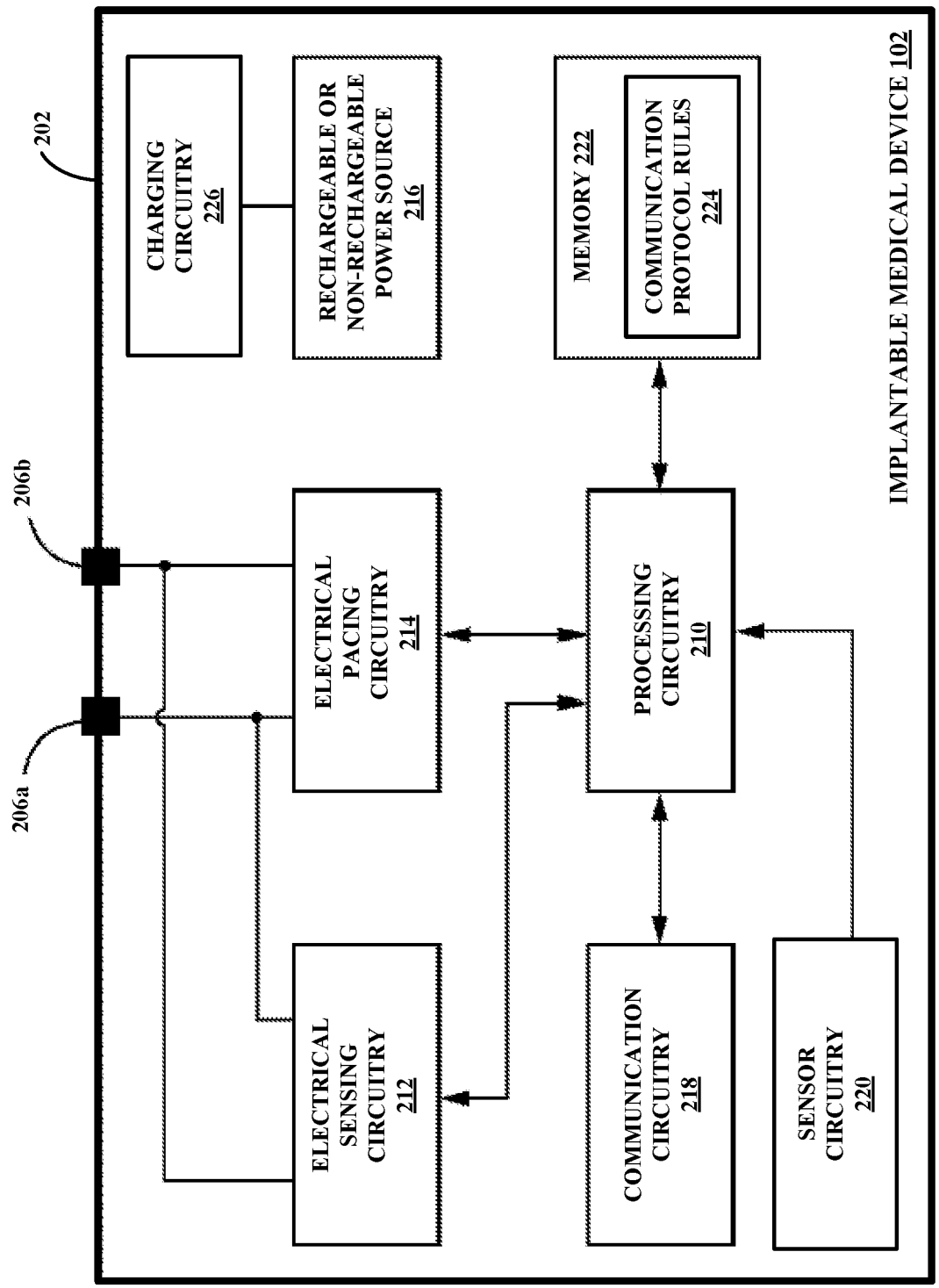
FIG. 3 shows the device of FIG. 2 in second detail according to the disclosure.

FIG. 2 shows an example configuration of a pacing device 102, which may correspond to atrial pacing device 102a and/or ventricular pacing device 102b of FIG. 1, and may be referred to more generally as an IMD 102 in first detail according to the disclosure. As illustrated, IMD 102 may be configured to include housing 202, fixation times 204a-d (collectively, "fixation tines 204"), and tip/ring electrodes 206a-b, respectively (collectively, "electrodes 206"). In practice, housing 202 may be configured so as to exhibit a size and form factor that permits IMD 102 to be entirely implanted within heart 108 (intracardiac) of patient 110, such as within right atrium 104 or right ventricle 106 (see FIG. 1).

Housing 202 may exhibit a cylindrical or pill-shaped form factor may in general be hermetically sealed to prevent ingress of fluid therein, and fixation tines 204 may be configured to extend from housing 202 and to engage with cardiac tissue to affix IMD 102 to a position within heart 108 of patient 110, e.g., at or near the apex of right ventricle 106 as shown in FIG. 1. Fixation tines 204 may be fabricated from any biologically inert material, such as a shape memory material (e.g., Nitinol). The number and configuration of fixation tines 204 illustrated in FIG. 2 is merely one example, and other numbers and configurations of fixation tines 204 for anchoring IMD 102 to cardiac or other tissue are contemplated. Additionally, although IMD 102 includes a plurality of fixation tines 204 that are configured to anchor IMD 102 to tissue, in other examples IMD 102 may be fixed to tissue using other types of fixation mechanisms, such as, but not limited to, barbs, coils, and the like.

FIG. 3 is a functional block diagram illustrating an example configuration of IMDs 102. The illustrated example is an example functional configuration of a leadless pacing device 102. In the illustrated example, IMD 102 may be configured to include processing circuitry 210, electrical sensing circuitry 212, electrical pacing circuitry 214, power source 216, which may be configured as a rechargeable or non-rechargeable battery, communication circuitry 218, sensor circuitry 220 and non-transitory memory 222, as illustrated in FIG. 3, to implement functionality attributable to a leadless pacemaker device, such as the Micra Transcatheter Pacing System from Medtronic Public Limited Company, of Fridley, Minn. (operational headquarters). Power source 216 may be coupled to charging circuitry 226 as shown in FIG. 3 when power source 216 is rechargeable, e.g., when IMD 102 is configured to include a rechargeable battery or supercapacitor. Although the present disclosure is not so limited, charging circuitry 226 may be configured to force current through power source 216 to recharge power source 216 periodically or at least intermittently as a function of demand on power source 216.

Examples of non-rechargeable (also referred to as "primary") power sources include batteries having a lithium-ion chemistry, such as lithium (Li) in combination with one or more of iodide ($I_2$), silver vanadium oxide (SVO), or carbon monofluoride (CFx). Examples of rechargeable power sources include batteries having a lithium-ion chemistry, such as lithium in combination with one or more oxides of nickel (Ni), manganese (Mn), or cobalt (Co). In general, IMD 102 when configured to exhibit either one of a rechargeable or non-rechargeable power source and when incorporated into system 100 may enable the features or aspects of the present disclosure.

For example, processing circuitry 210 of IMD 102 (equivalently, diagnostic device 112 or another IMD) may be configured to determine a state change of system 100. A state change may generally refer to any event that serves as stimulus for IMD 102 to respond to by taking action, such as onset of patient arrhythmia, or a communication request, or loss of inter-device synchronization, all as discussed further below, or any other event, such as detection of any physiological event or physiological change in the patient (e.g., change in A-V conduction, loss of capture), newly acquired physiological or device integrity data, expiration of a timer, or a process interrupt.

In general, the action taken in response to the state change may include switching an operational mode of IMD 102. As used herein, an operational mode refers to a set of respective values for one or more parameters or settings that control the operation of IMD 102, e.g., to sense physiological signals and deliver therapy. Each of a plurality of operational modes may have one or more of the values that differ from other operational modes. Different operational modes may include different values for pacing pulse magnitude, A-V, V-V, or other escape intervals, parameters that define a sensor-indicated pacing rate, whether a pacing mode that modifies escape intervals to facilitate intrinsic conduction is active, sensing thresholds, blanking interval, or any other interval, delay, or threshold. Example operational modes include pacing and sensing modes known in the art, such as the multi-chamber pacing and sensing modes discussed above (e.g., VDI, VDD, DDI, DDD, VDIR, VDDR, DDIR, DDDR, etc.). Different pacing and sensing modes may be different operational modes. However, different operational modes may in some cases have the same pacing and sensing mode, but different values for parameters or settings of that mode, or other operational parameters or settings of IMD 102 not necessarily related to the pacing and sensing mode.

In these and other examples, processing circuitry 210 may respond to the state change and operational mode switch by switching IMD 102 to a particular operational-mode-specific communication protocol 118 (see FIG. 1) based on a set of communication protocol rules 224 (see FIG. 3) as stored in non-transitory memory 222 of IMD 102. As mentioned above, a particular one operational-mode-specific communication protocol 118 may represent only one of a plurality of different communication protocols, each one associated with a corresponding one of communication protocol rules 224, that each may be defined such that level of power draw from power source 216 when configured as a non-rechargeable battery is less than level of power draw from power source 216 when configured as a rechargeable battery for IMD 102 to engage in inter-device communication within system 100.

As an example, and for any particular operational-mode-specific communication protocol, a ratio of power draw as defined with respect to sum total power draw for atrial pacing device 102a and ventricular pacing device 102b to engage in communication with each other, and with IMD 102 in this example corresponding to one or the other of atrial pacing device 102a and ventricular pacing device 102b, may be quantified as a 60.0%:40.0% (device 102a: device 102b) ratio, or as a 75.0%:25.0% ratio, or as a 90.0%:10.0% ratio, or even as a 97.0%:3.0% ratio, such that ventricular pacing device 102b is burdened substantially less than atrial pacing device 102a for the purpose of inter-device communication. Further, a particular ratio as described may be associated with a particular operational-mode-specific protocol. As an example, the 97.0%:3.0% ratio may be associated with a patient arrhythmia communication protocol for the IMD 102 to respond to a patient arrhythmia. In this example, there may be minimal communication between atrial pacing device 102a and ventricular pacing device 102b during the arrhythmic episode so that atrial pacing device 102a and ventricular pacing device 102b may immediately and without the burden of communicating with each other properly respond to the patient arrhythmia as intended, and most if any communication between atrial pacing device 102a and ventricular pacing device 102b may be handled by atrial pacing device 102a (as per 97.0%:3.0% ratio).

As another example, the 75.0%:25.0% ratio as mentioned may be associated with a loss of synchronization communication protocol for the IMD 102 to respond to loss of synchronization with another device in system 100 of FIG. 1. In this example, there may be slight communication between atrial pacing device 102a and ventricular pacing device 102b so that atrial pacing device 102a and ventricular pacing device 102b may re-establish synchronization, and some communication burden may be shared between atrial pacing device 102a and ventricular pacing device 102b. As another example, the 60.0%:40.0% ratio as mentioned may be associated with a data exchange communication protocol for ventricular pacing device 102b to respond to a request for communication with atrial pacing device 102a in system 100 of FIG. 1. In this example, there may be extensive communication between atrial pacing device 102a and ventricular pacing device 102b so that atrial pacing device 102a and ventricular pacing device 102b may communicate in a manner as intended, where communication burden may be more equally shared between atrial pacing device 102a and ventricular pacing device 102b. The data exchange communication protocol may in general represent any type of communication protocol other than the patient arrhythmia communication protocol and loss of synchronization communication protocol, and one of ordinary skill in the art will appreciate that many other examples are possible and that power draw ratio as contemplated throughout may be a function of a type of state change of system 100, as discussed further below in connection with at least FIGS. 4-5.

With reference now to FIG. 3 only, such elements of IMD 102 as illustrated in FIG. 3 may be realized as any combination of analog and digital circuitry, any combination of discrete and integrated circuitry, and any combination of software and firmware, to implement functions attributed to IMD 102 as discussed throughout. Such elements or circuitry may be implementation-specific and further may evolve as technology evolves. Non-transitory memory 222 in particular may store instructions, such as instructions corresponding to communication protocol rules 224, that when executed by processing circuitry 210 may cause processing circuitry 210 to monitor and/or control any particular one of electrical sensing circuitry 212, electrical pacing circuitry 214, power source 216, that may be configured as a rechargeable or non-rechargeable battery, communication circuitry 218 and sensor circuitry 220 to implement the features or aspects of the present disclosure.

As such, processing circuitry 210 may include any one or more of a microprocessor, a controller, a digital signal processor (DSP), an application specific integrated circuit (ASIC), a field-programmable gate array (FPGA), or equivalent discrete or integrated logic circuitry. In some examples, processing circuitry 210 may include multiple components, such as any combination of one or more microprocessors, one or more controllers, one or more DSPs, one or more ASICs, or one or more FPGAs, as well as other discrete or integrated logic circuitry. Additionally, although illustrated as separate functional components or elements in FIG. 3, some or all of the functionality attributed to electrical sensing circuitry 212, electrical pacing circuitry 214, communication circuitry 218 and sensor circuitry 220 may be implemented in the one or more combination of one or more microprocessors, one or more controllers, one or more DSPs, one or more ASICs, one or more FPGAs, and/or other discrete or integrated logic circuitry that may correspond to processing circuitry 210.

In practice, processing circuitry 210 may communicate with non-transitory memory 222 and, in addition to communication protocol rules 224, non-transitory memory 222 may include computer-readable instructions that, when executed by processing circuitry 210, cause processing circuitry 210 and any other components or circuitry of IMD 102 to perform various functions in a manner consistent with the features or aspects of the present disclosure, as would be understood by one of ordinary skill in the art of implantable medical devices. Non-transitory memory 222 may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other non-transitory memory device.

In the example of FIG. 3, electrical pacing circuitry 214 and electrical sensing circuitry 212 are electrically coupled to electrodes 206 and although not explicitly shown diagnostic circuitry 205 may be electrically coupled to electrodes 206 as well. Processing circuitry 210 may be configured to control electrical pacing circuitry 214 to generate and deliver pacing pulses to heart 108 (e.g., to right atrium 104 or right ventricle 106) of patient 110 via electrodes 206. In addition, processing circuitry 210 may be configured to control electrical sensing circuitry 212 to monitor an electrical signal from electrodes 206, which in practice act like an antenna, in order to monitor electrical activity of heart 108. Electrical sensing circuitry 212 may include circuits configured to acquire a signal from electrodes 206, as well as circuits to filter, amplify, and otherwise process the signal. The signal may represent intrinsic cardiac electrical activity, such as ventricular depolarizations and repolarizations and atrial depolarizations, and may be referred to as an electrical cardiac signal or a cardiac electrogram signal. Electrical sensing circuitry 212 may be configured to detect ventricular depolarizations, or ventricular activation events, within the electrical cardiac signal and detects atrial depolarizations, or atrial activation events, within the electrical cardiac signal.

Sensor circuitry 220 of IMD 102 may comprise one or more accelerometers. In some examples, sensor circuitry 220 comprises a plurality of accelerometers, e.g., three accelerometers, each of which is oriented to detect motion in the direction of a respective orthogonal axis or vector. In other examples, sensor circuitry 220 may comprises one or more different sensors that generate a signal as a function of motion, instead of or in addition to the one or more accelerometers, such as gyros, mercury switches, or bonded piezoelectric crystals. In other examples, sensor circuitry 220 may be realized as a pressure sensor instead of one or more accelerometers.

Communication circuitry 218 may include any suitable hardware (e.g., an antenna), firmware, software, or any combination thereof to enable IMD 102 to communicate with one or more of the devices as illustrated in FIG. 1. More specifically, under the control of processing circuitry 210, and based on instructions stored on or in non-transitory memory 222, and in particular based on communication protocol rules 224 in example implementations, communication circuitry 218 may receive downlink telemetry from, and send uplink telemetry to one or more of atrial pacing device 102a, ventricular pacing device 102b, diagnostic device 112 and programmer device 116 via an antenna included in communication circuitry 218. Thus, in practice, at least processing circuitry 210, non-transitory memory 222 and communication circuitry 218 may draw power from power source 216 for the purpose of IMD 102 to communicate with one or more other elements of system 100 of FIG. 1. And, similar to that as mentioned above, it may be desirable to minimize rate of depletion of power source 216 when realized as a non-rechargeable battery and thus extend the operational lifetime of IMD 102. An example method to minimize rate of depletion of power source 216 when realized as a non-rechargeable battery is discussed in connection with at least FIG. 4

Figure 4:
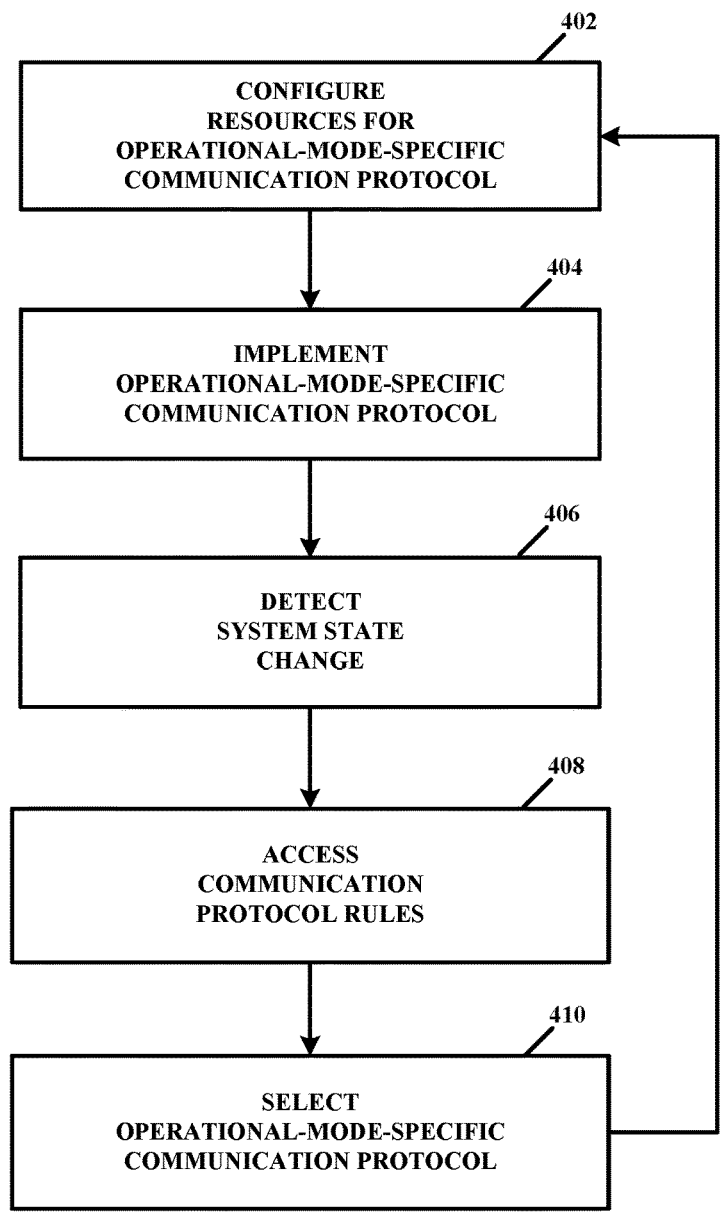
FIG. 4 shows a first example method according to the disclosure.

FIG. 4 shows a first example method 400 according to the disclosure, and is described from the perspective of IMD 102 of FIGS. 1-3. Thus, method 400 may be considered from the perspective of any one of atrial pacing device 102a, ventricular pacing device 102b and diagnostic device 112 of FIG. 1, and method 400 relates to an algorithm where at all times an operational-mode-specific communication protocol may be enforced whereby inter-device communication between IMD 102 and any one other device of FIGS. 1-3 is such that level of power draw from power source 216 of IMD 102 when configured as a non-rechargeable battery is less than level of power draw from the any one other device of FIGS. 1-3, that in the context of the present example may be configured to exhibit a power source realized as a rechargeable battery (i.e., any one device FIGS. 1-2 may be configured to exhibit a non-rechargeable or rechargeable power supply).

In the example of FIG. 4, a continuous loop is defined whereby IMD 102 may in sequence configure (step 402) its own resources, e.g., processing circuitry 210 of IMD 102 may configure its resources, to implement (step 404) a particular operational-mode-specific communication protocol, and then IMD 102 may detect (step 406) a state change of system 100 of FIG. 1, and access (step 408) communication protocol rules 224 from non-transitory memory 222 as shown in FIG. 3 to select (step 410), based on type of state change of system 100, another, different particular operational-mode-specific communication protocol to implement as required and as per the continuous loop. Such an algorithm as illustrated in FIG. 4 may be applicable to a large number of different scenarios.

As an example, IMD 102 may in practice be operating in an initial state as per an instant programmed mode that corresponds to any one of the following dual chamber and/or atrial tracking modes: VDI; VDD; DDI; DDD; VDIR; VDDR; DDIR; DDDR. In this example, each one of the mentioned dual chamber and/or atrial tracking modes may have a corresponding one operational-mode-specific communication protocol associated therewith, that in turn is associated with a corresponding one of communication rules 224 as stored within non-transitory memory 222 (see FIG. 3). If the instant programmed mode corresponds to DDDR, for example, then IMD 102 may configure (step 402) its own resources to implement (step 404) a particular operational-mode-specific communication protocol that is associated with mode DDDR and that, based on a corresponding one of communication rules 224 as accessed via from non-transitory memory, has a particular level of power draw for IMD 102 to enforce such that level of power draw from power source 216 of IMD 102, that is configured as a non-rechargeable battery, is less than level of power draw from any one other device of FIGS. 1-3, that in the context of the present example would be configured to exhibit a power source realized as a rechargeable battery. A ratio may be a convenient way to quantify such levels, similar to that discussed above.

As an example, a 85.0%:15.0% ratio may be associated with a DDDR protocol for the IMD 102 to implement DDDR mode. In this example, there may be some communication between IMD 102 and the any one other device of FIGS. 1-3, whereby the majority of the communication budget in terms of power consumption may be assigned to the any one other device of FIGS. 1-3. In this manner, operational lifetime of IMD 102 may be extended because load on the non-rechargeable power source may be substantially reduced over time.

Regarding the prior example, such an implementation is applicable to each one of the listed dual chamber and/or atrial tracking modes. Further, it is contemplated that level of power draw from power source 216 by IMD 102 may be precisely controlled by IMD 102 by disabling communication circuitry 218 for a particular time interval (e.g., modulating radio power on/off), by controlling extent of communication from IMD 102 to the any one other device of FIGS. 1-3 over any particular time interval, by throttling processing circuitry 210 to not perform certain communication-related functions over any particular time interval, and so on. Then, IMD 102 may detect (step 406) a state change of system 100 of FIG. 1, and access (step 408) communication protocol rules 224 from non-transitory memory 222 as shown in FIG. 3 to select (step 410), based on type of state change of system 100, another particular operational-mode-specific communication protocol to implement as per the continuous loop. An example method to select another particular operational-mode-specific communication protocol based on type of state change of system 100 is discussed in connection with at least FIG. 5.

Figure 5:
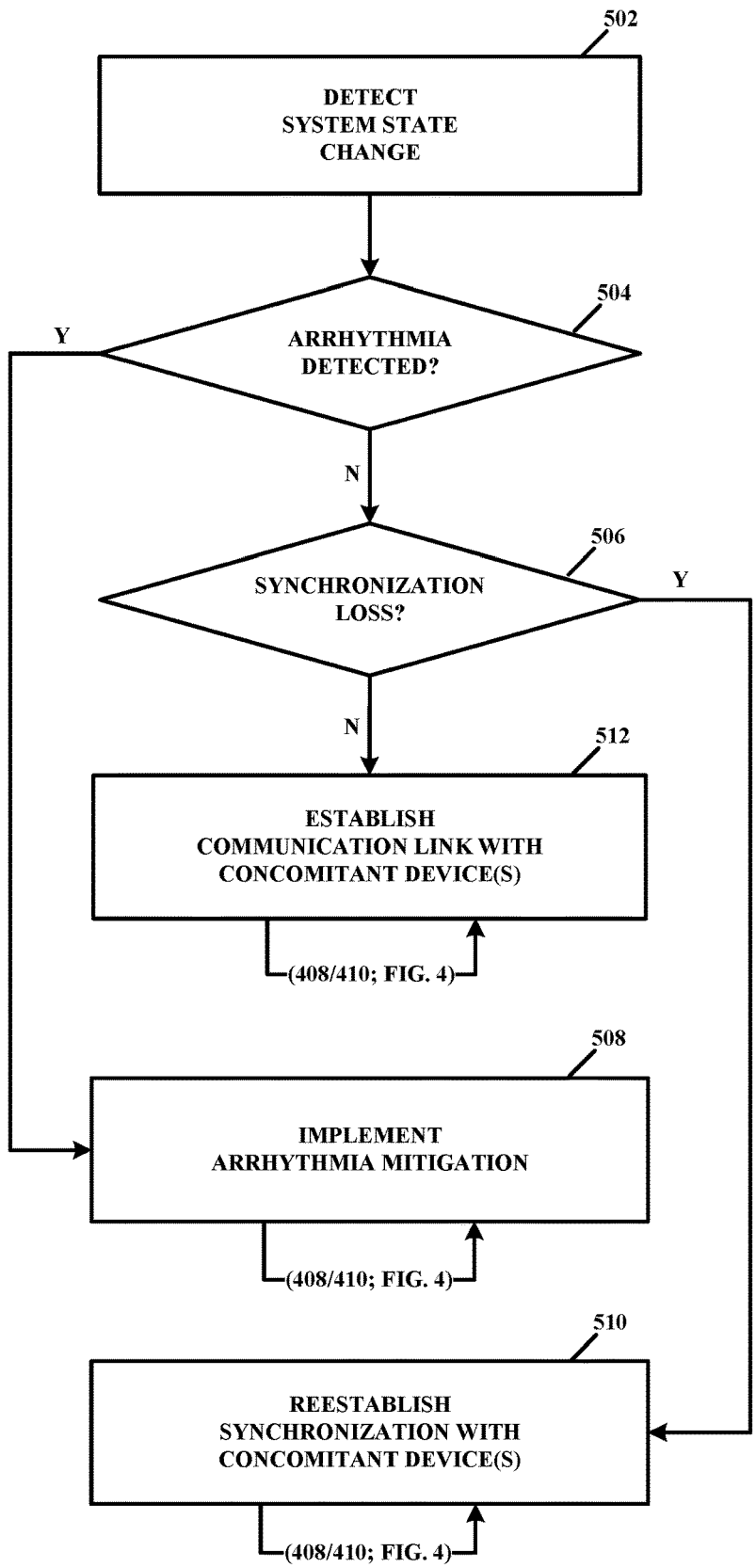
FIG. 5 shows a second example method according to the disclosure.

FIG. 5 shows a second example method 500 according to the disclosure, and method 500 may be considered an extension of, or a supplement to, method 400 of FIG. 4. Thus, method 500 may be considered as from the perspective of any one of atrial pacing device 102a, ventricular pacing device 102b and diagnostic device 112 of FIG. 1, and relates to an algorithm where an operational-mode-specific communication protocol may be enforced whereby inter-device communication between IMD 102 and any one other device of FIGS. 1-3 is such that level of power draw from power source 216 of IMD 102 when configured as a non-rechargeable battery is less than level of power draw from the any one other device of FIGS. 1-3, that in the context of the present example may be configured to exhibit a power source realized as a rechargeable battery (i.e., any one device FIGS. 1-2 may be configured to exhibit a non-rechargeable or rechargeable power supply).

In the example of FIG. 5, a continuous loop is defined, as method 500 may be considered an extension of, or a supplement to, method 400 of FIG. 4, whereby IMD 102 may in sequence detect (step 502) a state change of system 100 of FIG. 1, and then determine whether a type of the state change corresponds to detection of a patient arrhythmia (step 504) or detection of loss of synchronization (step 506) between IMD 102 and the any one other device of FIGS. 1-3. If, for example, a type of the state change corresponds to detection of a patient arrhythmia, as detected via electrical sensing circuitry 212 of IMD 102 (see FIG. 3), then flow within method 500 may branch such that IMD 102 may implement measures (e.g., pacing, defib, etc.) to mitigate the patient arrhythmia (step 508). As part of such measures, IMD 102 may access (step 408; FIG. 4) communication protocol rules 224 from non-transitory memory 222 as shown in FIG. 3 to select (step 410; FIG. 4), based on a type of state change of system 100 that corresponds to detection of a patient arrhythmia, a patient arrhythmia communication protocol that is associated with a corresponding one of communication rules 224 as stored within non-transitory memory 222, to enforce level of power draw from power source 216 of IMD 102, that is configured as a non-rechargeable battery, to a level that is less than level of power draw from any one other device of FIGS. 1-3.

As an example, a 95.0%:5.0% ratio may be associated with a patient arrhythmia protocol for the IMD 102 to mitigate the patient arrhythmia. In this example, there may be minimal communication between IMD 102 and the any one other device of FIGS. 1-3, whereby the vast majority of the communication budget in terms of power consumption may be assigned to the any one other device of FIGS. 1-3. In this manner, operational lifetime of IMD 102 may be extended because load on the non-rechargeable power source may be substantially reduced over time.

If, however, a type of the state change corresponds to detection of a loss of synchronization with the any one other device of FIGS. 1-3, as determined by processing circuitry 210 via ongoing (but limited) communication with the any one other device of FIGS. 1-3, then flow with method 500 may branch such that IMD 102 may implement measures (e.g., a predefined communication sequence) to reestablish synchronization with the any one other device of FIGS. 1-3 (step 510). As part of such measures, IMD 102 may access (step 408; FIG. 4) communication protocol rules 224 from non-transitory memory 222 as shown in FIG. 3 to select (step 410; FIG. 4), based on a type of state change of system 100 that corresponds to loss of synchronization, a loss of synchronization communication protocol that is associated with a corresponding one of communication rules 224 as stored within non-transitory memory 222 to enforce level of power draw from power source 216 of IMD 102, that is configured as a non-rechargeable battery, to a level that is less than level of power draw from any one other device of FIGS. 1-3.

As an example, a 70.0%:30.0% ratio may be associated with a loss of synchronization protocol for the IMD 102 to mitigate the loss of synchronization. In this example, there may be some communication between IMD 102 and the any one other device of FIGS. 1-3, whereby the majority of the communication budget in terms of power consumption may be assigned to the any one other device of FIGS. 1-3. In this manner, operational lifetime of IMD 102 may be extended because load on the non-rechargeable power source may be substantially reduced over time.

If, however, a type of the state change does not correspond to either one of detection of a patient arrhythmia or loss of synchronization, then flow within method 500 may branch such that IMD 102 may instantiate a data exchange communication protocol, that may in general represent any type of communication protocol other than the patient arrhythmia communication protocol and loss of synchronization communication protocol, to establish a communication link with the any one other device of FIGS. 1-3 (step 512). As part of such measures, IMD 102 may access (step 408; FIG. 4) communication protocol rules 224 from non-transitory memory 222 as shown in FIG. 3 to select (step 410; FIG. 4), based on a type of state change of system 100 that corresponds to general data exchange that is associated with a corresponding one of communication rules 224 as stored within non-transitory memory 222, to enforce level of power draw from power source 216 of IMD 102, that is configured as a non-rechargeable battery, to a level that is less than level of power draw from any one other device of FIGS. 1-3.

As an example, a 60.0%:40.0% ratio may be associated with a data exchange protocol for the IMD 102 to open a communication link between IMD 102 and the any one other device of FIGS. 1-3. In this example, there may be substantial communication between IMD 102 and the any one other device of FIGS. 1-3, whereby the communication budget in terms of power consumption may be approximately shared between IMD 102 and the any one other device of FIGS. 1-3 but the more substantial burden is still on the any one other device of FIGS. 1-3. In this manner, operational lifetime of IMD 102 may be extended because load on the non-rechargeable power source may be substantially reduced over time. In this manner, the algorithm of FIG. 4, as well as FIG. 5, may be applicable to a large number of different scenarios but still other examples are contemplated.

Figure 6:
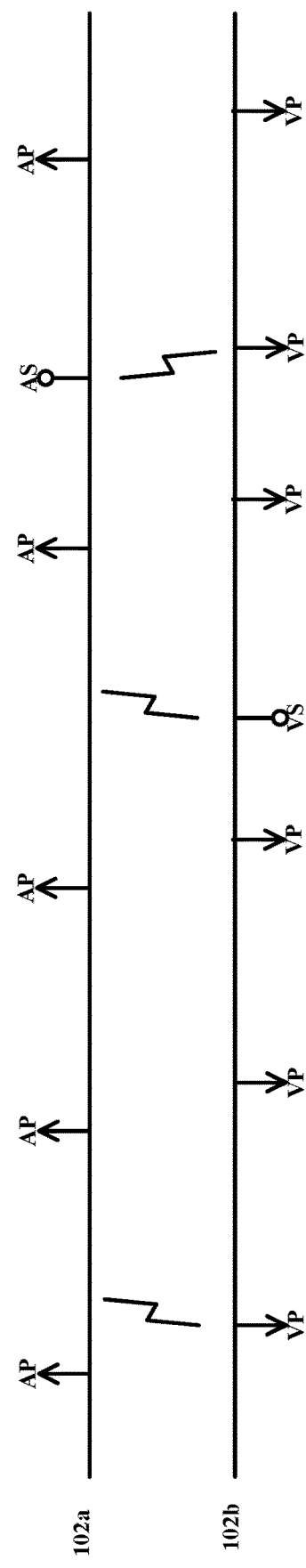
FIG. 6 shows a first example timing diagram according to the disclosure.
Figure 7:
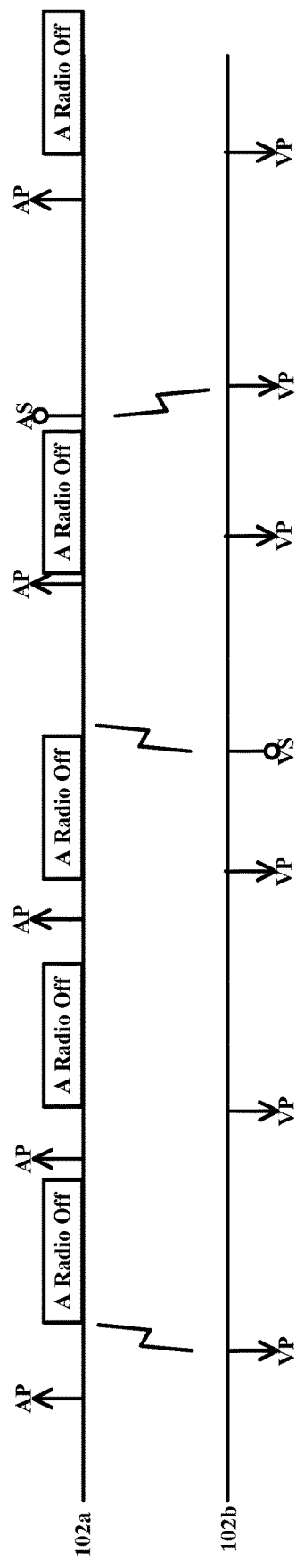
FIG. 7 shows a second example timing diagram according to the disclosure.
Figure 8:
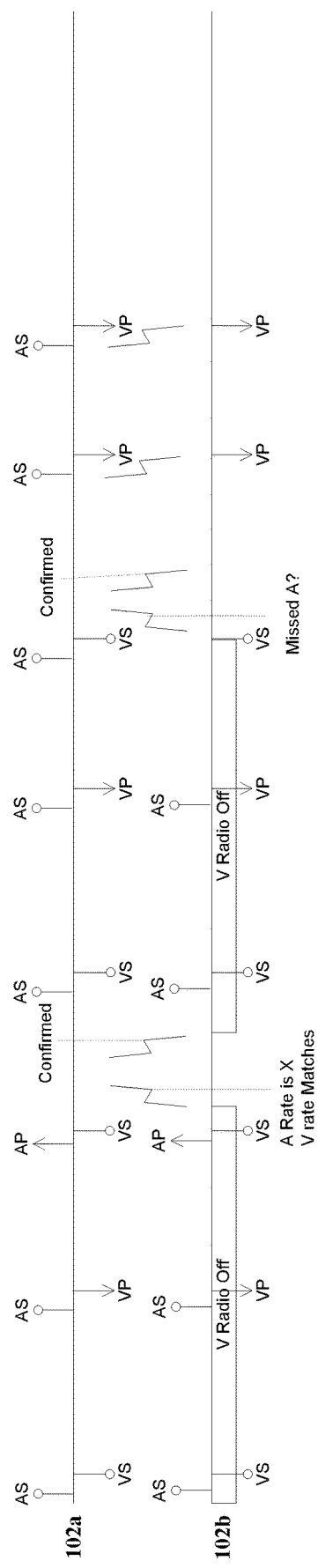
FIG. 8 shows a third example timing diagram according to the disclosure.

For example, FIG. 6 shows a first example timing diagram 600 according to the disclosure. FIG. 7 shows a second example timing diagram 700 according to the disclosure. FIG. 8 shows a third example timing diagram 800 according to the disclosure. In each one of FIGS. 6-8, actions associated with atrial pacing device 102*a*, configured to include or exhibit a rechargeable battery, are represented along an upper-positioned time axis, and actions associated with ventricular pacing device 102*b*, configured to include or exhibit a non-rechargeable battery, are represented along a lower-positioned time axis. It is contemplated that such a system with a life-saving device with a primary cell battery (non-rechargeable) and one or more devices with rechargeable batteries confers advantages in addition or as a complement to that discussed above.

For example, patients are protected by the primary cell battery and are likely to (at worst) become symptomatic if the rechargeable battery depletes. Patients can be instructed to check/charge their battery if they feel certain symptoms, which a physician can provoke by temporarily disabling the device(s) with the rechargeable batteries. As another example, devices can be set to pacing modes that minimize the use of the primary cell battery, such as a minimized RV pacing mode, to maximize the operational life of the primary cell life-saving device. The primary cell life-saving device can further be placed into a "backup" mode or a "symptom provoking mode" if there is evidence that the rechargeable device has a low battery, such as a VVI 40 or VVI 65 pacing mode.

As another example, communication between the devices can be duty cycled so that the primary cell device uses a minimal amount of energy on communication, while the rechargeable device has a larger communication energy budget, for example if the communication protocol is such that listening is more expensive than occasionally broadcasting then the primary cell battery device can spend most of its time with its radio OFF, only waking to talk, and occasionally listen. The rechargeable device can spend most of its time with the radio ON, in listening mode. If the communication protocol is such that listening is cheaper than occasionally talking, then the V device (ventricular pacing device 102b) could have its radio in listening mode and the A device (atrial pacing device 102a) could be responsible for waking up to talk occasionally.

As another example, a differentiation between "full listen" and a low power "trigger" listen mode may be realized so that a device can have its radio draining a minimal amount of power but still respond if a pace is needed. For example, if an AS (atrial sense) occurs in DDD mode, the V device should be woken up to pace, but otherwise has no need to listen. As another example, ability to determine and configure transmissions and listening based on device and patient characteristics. Pacing mode and device history may change whether listening or talking is cheaper. For example, a patient that is primarily A paced-V paced at a lower rate may have very little need for communication, so the talking budget may be relatively low. The listening device should or could be the A device, consistent with description provided above in connection with FIGS. 1-5 where communication rules may be changed based on pacing mode. Such an implementation is further demonstrated in FIG. 6 where atrial pacing device 102a is always listening and sends a conditional trigger only on AS where V-V timing should be affected. Ventricular pacing device 102b communicates with atrial pacing device 102a to indicate when a next AP (atrial pace) should occur and may only communicate if A-A time has changed.

As another example, as demonstrated in FIG. 7, all radios may be OFF during agreed upon times, such as during blanking or certain refractory periods, when no events could cause one device to need to communicate to another. If needed, information about what occurred while the radios were OFF may be broadcast at the end of the OFF period, such as if a ventricular event occurred during PVARP (Post Ventricular Atrial Refractory Period) so that PVARP should restart.

As another example, as demonstrated in FIG. 8, communication budgets may be further reduced if the devices are able to synchronize by cross-chamber sensing, and only communicate when cross-chamber sensing becomes unreliable or a special exception case occurs, such as during a programming session, a temporary nightly test or some other major change. Small amounts of data can be sent periodically to minimize communication, for example the A device could send an observed cross-chamber V rate that it has calculated to the V device to confirm that cross-chamber sensing is functional. In this situation, the A device could wait to see if it sensed a V event where expected and send a "pace now" trigger if it didn't see a V event in the expected window, which the V device could ignore if it did see a V event.

As discussed above in connection with FIGS. 1-8, the features or aspects of the present disclosure address many technical challenges in example implementations in which a first implantable medical device is configured with a rechargeable power source and a second implantable medical device is configured with a non-rechargeable power source. For example, it is contemplated that in practice an operational-mode-specific communication protocol may be enforced whereby inter-device communication between the first implantable medical device and the second implantable medical device is such that level of power draw from the rechargeable power source by the first implantable medical device is greater than level of power draw from the non-rechargeable power source by the second implantable medical device. As such, and as demonstrated by one or more of the following numbered examples, one of ordinary skill in the art will understand that many benefits and advantages flow the features or aspects of the present disclosure.

Example 1

A system comprising: a first implantable leadless pacing device that includes a rechargeable power source housed therein; and a second implantable leadless pacing device that includes a non-rechargeable power source housed therein; wherein the first implantable leadless pacing device and the second implantable leadless pacing device are configured to operate together as a multi-chamber pacing system according to a programmed operational mode, and wherein the first implantable leadless pacing device and the second implantable leadless pacing device are configured to communicate according to a communication protocol that is specific to the programmed operational mode.

Although not so limited, such an example implementation is consistent with that shown and described in connection with at least FIG. 1 with reference to at least atrial pacing device 102a and ventricular pacing device 102b, wherein an example of a rechargeable power source includes a nickel-cadmium-based battery and an example of a non-rechargeable power source includes a lithium-iodine-based battery, although many different types of rechargeable and non-rechargeable batteries exist and battery types may evolve as technology evolves. In such and other examples, a particular communication protocol may represent only one of a plurality of different communication protocols that each may be defined such that level of power draw from a power source when configured as a non-rechargeable battery is less than level of power draw from power source when configured as a rechargeable battery for IMD 102 to engage in inter-device communication within system 100. Additionally, a particular communication protocol in general may be specific to an operational mode where pacing settings for the operational mode may represent or correspond to any one or combination of a particular pacing mode (e.g., DDD), a particular pacing rate (e.g., 65 beats per minute), a particular refractory setting (e.g., t=1 millisecond), a particular blanking setting (e.g., t=5 milliseconds), etc., as would be understood by one of ordinary skill in the art. Other examples are possible.

Example 2

The system of Example 1, wherein level of power draw from the rechargeable power source by the first implantable leadless pacing device is greater than level of power draw from the non-rechargeable power source by the second implantable leadless pacing device for the communication protocol. Although not so limited, such an example implementation is consistent with that shown and described in connection with at least FIG. 1 with reference to at least atrial pacing device 102a and ventricular pacing device 102b, wherein for any particular operational-mode-specific communication protocol a ratio of power draw as defined with respect to sum total power draw for atrial pacing device 102a and ventricular pacing device 102b to engage in communication with each other may be quantified as a 60.0%:40.0% (device 102a:device 102b) ratio, or as a 75.0%:25.0% ratio, or as a 90.0%:10.0% ratio, or even as a 97.0%:3.0% ratio. Other examples are possible.

Example 3

The system of any one of Examples 1-2, wherein the programmed operation mode is one of a plurality of operation modes, and wherein the first and second implantable leadless pacing devices are configured to switch between ones of the plurality of operational modes in response to a loss of synchronization between the first and second implantable leadless pacing devices as detected by at least one of the first and second implantable leadless pacing devices. Although not so limited, such an example implementation is consistent with that shown and described in connection with at least FIG. 5 with reference to at least atrial pacing device 102a and ventricular pacing device 102b, wherein a state change may correspond to loss of synchronization between atrial pacing device 102a and ventricular pacing device 102b. Other examples are possible.

Example 4

The system of any one of Examples 1-3, wherein the programmed operation mode is one of a plurality of operation modes, and wherein the first and second implantable leadless pacing devices are configured to switch between ones of the plurality of operational modes in response to an onset of patient arrhythmia as detected by at least one of the first and second implantable leadless pacing devices. Although not so limited, such an example implementation is consistent with that shown and described in connection with at least FIG. 5 with reference to at least atrial pacing device 102a and ventricular pacing device 102b, wherein a state change may correspond to detection of onset of patient arrhythmia. Other examples are possible.

Example 5

The system of any one of Examples 1-4, wherein the programmed operation mode is one of a plurality of operation modes, and wherein the first and second implantable leadless pacing devices are configured to switch between ones of the plurality of operational modes in response to a cessation of a patient arrhythmia as detected by at least one of the first and second implantable leadless pacing devices. Although not so limited, such an example implementation is consistent with that shown and described in connection with at least FIG. 5 with reference to at least atrial pacing device 102a and ventricular pacing device 102b, wherein a state change may correspond to detection of cessation of patient arrhythmia. Other examples are possible.

Example 6

The system of any one of Examples 1-5, further comprising a diagnostic monitor device that includes a non-rechargeable power source housed therein, and wherein the diagnostic monitor device is configured to communicate with at least one of the first and second implantable leadless pacing devices according to the communication protocol. Although not so limited, such an example implementation is consistent with that shown and described in connection with at least FIG. 1 with reference to at least diagnostic device 112. Other examples are possible.

Example 7

An implantable medical device comprising: a power source that is configured as one of a rechargeable power source or a non-rechargeable power source; electrical pacing circuitry that is coupled to the power source and that is configured to deliver cardiac pacing; communication circuitry that is coupled to the power source and configured to establish a communication link with an other implantable medical device that is arranged in a multi-chamber pacing system with the implantable medical device; and processing circuitry that is coupled to the power source, the electrical pacing circuitry and the communication circuitry, wherein the processing circuitry is configured to: determine a state change of the system, and switch between ones of a plurality of different communication protocols for the implantable medical device to operate according to and in which power draw from the power source for inter-device communication with the other implantable medical device is selected according to an operational mode for at least one of the implantable medical device and the implantable medical device to respond to the state change of the system; wherein a power source of the other implantable medical device is configured as the other one of the rechargeable power source or the non-rechargeable power source and each one of the plurality of different communication protocols is defined such that level of power draw from the non-rechargeable power source is less than level of power draw from the rechargeable power source for inter-device communication between the implantable medical device and the other implantable medical device.

Although not so limited, such an example implementation is consistent with that shown and described in connection with at least FIG. 1 with reference to at least atrial pacing device 102a and ventricular pacing device 102b, wherein many different types of rechargeable and non-rechargeable batteries exist and battery types may evolve as technology evolves. Additionally, a particular communication protocol may represent only one of a plurality of different communication protocols that each may be defined such that level of power draw from a power source when configured as a non-rechargeable battery is less than level of power draw from power source when configured as a rechargeable battery for IMD 102 to engage in inter-device communication within system 100. Moreover, a particular communication protocol in general may be specific to an operational mode where pacing settings for the operational mode may represent or correspond to any one or combination of a particular pacing mode, a particular pacing rate, a particular refractory setting, a particular blanking setting, etc., as would be understood by one of ordinary skill in the art. Other examples are possible.

Example 8

The device of Example 7, wherein the processing circuitry is configured to determine onset of loss of synchronization with the other implantable medical device as the state change of the system and to switch to a resynchronization communication protocol in which power draw from the rechargeable power source or the non-rechargeable power source of the implantable medical device is adjusted to a level that is specific to a resynchronization operational mode for the implantable medical device and the other implantable medical device to respond to the loss of synchronization. Although not so limited, such an example implementation is consistent with that shown and described in connection with at least FIG. 5 with reference to at least atrial pacing device 102*a* and ventricular pacing device 102*b*, wherein a state change may correspond to loss of synchronization between atrial pacing device 102*a* and ventricular pacing device 102*b* similar to that discussed above in connection with Example 3. Other examples are possible.

Example 9

The device of any one of Examples 7-8, wherein the processing circuitry is configured to determine onset of a patient arrhythmia as the state change of the system and to switch to a therapy delivery communication protocol in which power draw from the rechargeable power source or the non-rechargeable power source of the implantable medical device is adjusted to a level that is specific to a therapy delivery operational mode for the implantable medical device and the other implantable medical device to respond to the patient arrhythmia. Although not so limited, such an example implementation is consistent with that shown and described in connection with at least FIG. 5 with reference to at least atrial pacing device 102*a* and ventricular pacing device 102*b*, wherein a state change may correspond to detection of onset of patient arrhythmia similar to that discussed above in connection with Example 4. Other examples are possible.

Example 10

The device of any one of Examples 7-9, wherein the processing circuitry is configured to determine receipt of a request from the other implantable medical device as the state change of the system and to switch to a data exchange communication protocol in which power draw from the rechargeable power source or the non-rechargeable power source of the implantable medical device is adjusted to a level that is specific to a data exchange operational mode for the implantable medical device to respond to the request. Although not so limited, such an example implementation is consistent with that shown and described in connection with at least FIG. 5 with reference to at least atrial pacing device 102*a* and ventricular pacing device 102*b*, wherein a state change may correspond to loss of synchronization between atrial pacing device 102*a* and ventricular pacing device 102*b*, and a particular data exchange communication mode or protocol may subsequently be enforced. Other examples are possible.

Example 11

The device of any one of Examples 7-10, wherein the implantable medical device is configured as a leadless ventricular pacing device or a leadless atrial pacing device. Although not so limited, such an example implementation is consistent with that shown and described in connection with at least FIG. 1 with reference to at least atrial pacing device 102*a* and ventricular pacing device 102*b*. Other examples are possible.

Example 12

A system comprising: a first medical device that is configured to be implanted in a patient and to draw power from a rechargeable battery housed therein for inter-device communication; and a second medical device that is configured to be implanted in the patient and to draw power from a non-rechargeable battery housed therein for inter-device communication, wherein, responsive to a detected state change of the system, the second medical device is further configured to switch to a communication protocol in which power draw from the non-rechargeable battery for inter-device communication with the first medical device is selected according to operational mode programmed to at least one the first and second medical device.

Although not so limited, such an example implementation is consistent with that shown and described in connection with at least FIG. 1 with reference to at least atrial pacing device 102*a* and ventricular pacing device 102*b*, wherein many different types of rechargeable and non-rechargeable batteries exist and battery types may evolve as technology evolves. Additionally, a particular communication protocol may represent only one of a plurality of different communication protocols that each may be defined such that level of power draw from a power source when configured as a non-rechargeable battery is less than level of power draw from power source when configured as a rechargeable battery for IMD 102 to engage in inter-device communication within system 100. Moreover, a particular communication protocol in general may be specific to an operational mode where pacing settings for the operational mode may represent or correspond to any one or combination of a particular pacing mode, a particular pacing rate, a particular refractory setting, a particular blanking setting, etc., as would be understood by one of ordinary skill in the art. Other examples are possible.

Example 13

The system of Example 12, wherein the first medical device is configured as a leadless atrial pacing device and the second medical device is configured as a leadless ventricular pacing device. Although not so limited, such an example implementation is consistent with that shown and described in connection with at least FIG. 1 with reference to at least atrial pacing device 102*a* and ventricular pacing device 102*b*. Other examples are possible.

Example 14

The system of any one of Examples 12-13, wherein the first medical device is configured as a leadless right ventricular pacing device and the second medical device is configured as a leadless left ventricular pacing device or wherein the first medical device is configured as a leadless left ventricular pacing device and the second medical device is configured as a leadless right ventricular pacing device. Although not so limited, such an example implementation is consistent with that shown and described in connection with at least FIG. 1 with reference to at least atrial pacing device 102*a* and ventricular pacing device 102*b*. Other examples are possible.

Example 15

The system of any one of Examples 12-14, further comprising a third medical device configured to be implanted in the patient and to draw power from a non-rechargeable battery housed therein for inter-device communication, and wherein the third medical device is configured as a diagnostic monitor device and each one of the first medical device and the second medical device is configured as a leadless pacing device. Although not so limited, such an example implementation is consistent with that shown and described in connection with at least FIG. 1 with reference to at least atrial pacing device 102a, ventricular pacing device 102b and diagnostic device 112. Other examples are possible.

Example 16

The system of any one of Examples 12-15, wherein the second medical device is configured to detect loss of synchronization with the first medical device as the state change of the system and to switch to a resynchronization communication protocol in which power draw from the non-rechargeable battery for inter-device communication with the first medical device is adjusted to a level that is specific to a resynchronization operational mode for the first and second medical device to respond to the loss of synchronization and that is less than in magnitude power draw from the rechargeable battery by the first medical device in the resynchronization operational mode for inter-device communication. Although not so limited, such an example implementation is consistent with that shown and described in connection with at least FIG. 5 with reference to at least atrial pacing device 102a and ventricular pacing device 102b, wherein a state change may correspond to loss of synchronization between atrial pacing device 102a and ventricular pacing device 102b. Other examples are possible.

Example 17

The system of any one of Examples 12-16, wherein the second medical device is configured to detect a patient arrhythmia as the state change of the system and to switch to a therapy delivery communication protocol in which power draw from the non-rechargeable battery for inter-device communication with the first medical device is adjusted to a level that is specific to a therapy delivery operational mode for the first and second medical device to respond to the patient arrhythmia and that is less than in magnitude power draw from the rechargeable battery by the first medical device in the therapy delivery operational mode for inter-device communication. Although not so limited, such an example implementation is consistent with that shown and described in connection with at least FIG. 5 with reference to at least atrial pacing device 102a and ventricular pacing device 102b, wherein a state change may correspond to detection of onset of patient arrhythmia. Other examples are possible.

Example 18

The system of any one of Examples 12-17, wherein the second medical device is configured to detect a request from the first medical device to communicate as the state change of the system and to switch to a data exchange communication protocol in which power draw from the non-rechargeable battery for inter-device communication with the first medical device is adjusted to a level that is specific to a data exchange operational mode for the second medical device to respond to the request and that is less than in magnitude power draw from the rechargeable battery by the first medical device in the data exchange operational mode for inter-device communication. Although not so limited, such an example implementation is consistent with that shown and described in connection with at least FIG. 5 with reference to at least atrial pacing device 102a and ventricular pacing device 102b, wherein a state change may correspond to loss of synchronization between atrial pacing device 102a and ventricular pacing device 102b, and a particular data exchange communication mode or protocol may subsequently be enforced. Other examples are possible.

Example 19

The system of any one of Examples 12-18, wherein level of power draw from the non-rechargeable battery by the second device for inter-device communication with the first medical device is less than level of power draw from the rechargeable battery by the first device for inter-device communication with the second medical device for each one of a plurality of different communication protocols that each one of the first and second medical device is configured to execute for inter-device communication. Although not so limited, such an example implementation is consistent with that shown and described in connection with at least FIG. 1 with reference to at least atrial pacing device 102a and ventricular pacing device 102b, wherein for any particular operational-mode-specific communication protocol a ratio of power draw as defined with respect to sum total power draw for atrial pacing device 102a and ventricular pacing device 102b to engage in communication with each other may be quantified as a 60.0%:40.0% (device 102a:device 102b) ratio, or as a 75.0%:25.0% ratio, or as a 90.0%:10.0% ratio, or even as a 97.0%:3.0% ratio. Other examples are possible.

Example 20

The system of any one of Examples 12-19, wherein level of power draw from the non-rechargeable battery by the second device for inter-device communication with the first medical device is of magnitude to maximize operational lifetime of the non-rechargeable battery. Although not so limited, such an example implementation is consistent with that shown and described in connection with at least FIG. 1 with reference to at least atrial pacing device 102a and ventricular pacing device 102b, wherein such an example implementation is further consistent with one or more benefits or advantages of the present disclosure that relates to minimization of rate of depletion of a non-rechargeable power source and by extension an increase in operational lifetime of an implantable medical device configured to include the non-rechargeable power source. Other examples are possible.

Various examples have been described. These and other examples are within the scope of the following claims.

What is claimed is:
1. A system comprising:
a first implantable leadless pacing device that includes a rechargeable power source housed therein; and
a second implantable leadless pacing device that includes a non-rechargeable power source housed therein;
wherein the first implantable leadless pacing device and the second implantable leadless pacing device are configured to operate together as a multi-chamber pacing system according to a programmed operational mode of a set of operational modes,
wherein the first implantable leadless pacing device and the second implantable leadless pacing device are configured to communicate according to a communication protocol of a set of communication protocols that is specific to the programmed operational mode,
wherein the set of operational modes includes two or more operational modes, wherein each operational mode of the set of operational modes indicates a set of chambers in which to deliver pacing pulses using one or both of the first implantable leadless pacing device and the second implantable leadless pacing device and indicates a set of chambers in which to sense cardiac signals using one or both of the first implantable leadless pacing device and the second implantable leadless pacing device, and wherein the set of communication protocols comprises two or more communication protocols.

2. The system of claim 1, wherein level of power draw from the rechargeable power source by the first implantable leadless pacing device is greater than level of power draw from the non-rechargeable power source by the second implantable leadless pacing device for the communication protocol.

3. The system of claim 1, wherein the first and second implantable leadless pacing devices are configured to switch between ones of the set of operational modes in response to a loss of synchronization between the first and second implantable leadless pacing devices as detected by at least one of the first and second implantable leadless pacing devices.

4. The system of claim 1, wherein the first and second implantable leadless pacing devices are configured to switch between ones of the set of operational modes in response to an onset of patient arrhythmia as detected by at least one of the first and second implantable leadless pacing devices.

5. The system of claim 1, wherein the first and second implantable leadless pacing devices are configured to switch between ones of the set of operational modes in response to a cessation of a patient arrhythmia as detected by at least one of the first and second implantable leadless pacing devices.

6. The system of claim 1, further comprising a diagnostic monitor device that includes a non-rechargeable power source housed therein, and wherein the diagnostic monitor device is configured to communicate with at least one of the first and second implantable leadless pacing devices according to the communication protocol.

7. An implantable medical device comprising:
a power source that is configured as one of a rechargeable power source or a non-rechargeable power source;
electrical pacing circuitry that is coupled to the power source and that is configured to deliver cardiac pacing;
communication circuitry that is coupled to the power source and configured to establish a communication link with another implantable medical device that is arranged in a multi-chamber pacing system with the implantable medical device; and
processing circuitry that is coupled to the power source, the electrical pacing circuitry and the communication circuitry, wherein the processing circuitry is configured to:
determine a state change of the system, and
switch between ones of a set of communication protocols for the implantable medical device to operate according to and in which power draw from the power source for inter-device communication with the other implantable medical device is selected according to an operational mode of a set of operational modes for at least one of the implantable medical device and the implantable medical device to respond to the state change of the system,
wherein the set of operational modes includes two or more operational modes,
wherein the set of communication protocols comprises two or more communication protocols, and wherein a power source of the other implantable medical device is configured as the other one of the rechargeable power source or the non-rechargeable power source and each one of the plurality of different communication protocols is defined such that level of power draw from the non-rechargeable power source is less than level of power draw from the rechargeable power source for inter-device communication between the implantable medical device and the other implantable medical device.

8. The device of claim 7, wherein the processing circuitry is configured to determine onset of loss of synchronization with the other implantable medical device as the state change of the system and to switch to a resynchronization communication protocol of the set of communication protocols in which power draw from the rechargeable power source or the non-rechargeable power source of the implantable medical device is adjusted to a level that is specific to a resynchronization operational mode of the set of operational modes for the implantable medical device and the other implantable medical device to respond to the loss of synchronization.

9. The device of claim 7, wherein the processing circuitry is configured to determine onset of a patient arrhythmia as the state change of the system and to switch to a therapy delivery communication protocol of the set of communication protocols in which power draw from the rechargeable power source or the non-rechargeable power source of the implantable medical device is adjusted to a level that is specific to a therapy delivery operational mode of the set of operational modes for the implantable medical device and the other implantable medical device to respond to the patient arrhythmia.

10. The device of claim 7, wherein the processing circuitry is configured to determine receipt of a request from the other implantable medical device as the state change of the system and to switch to a data exchange communication protocol of the set of communication protocols in which power draw from the rechargeable power source or the non-rechargeable power source of the implantable medical device is adjusted to a level that is specific to a data exchange operational mode of the set of operational modes for the implantable medical device to respond to the request.

11. The device of claim 7, wherein the implantable medical device is configured as a leadless ventricular pacing device or a leadless atrial pacing device.

12. A system comprising:
a first medical device that is configured to be implanted in a patient and to draw power from a rechargeable battery housed therein for inter-device communication; and
a second medical device that is configured to be implanted in the patient and to draw power from a non-rechargeable battery housed therein for inter-device communication,
wherein, responsive to a detected state change of the system, the second medical device is further configured to switch to a communication protocol of a set of communication protocols in which power draw from the non-rechargeable battery for inter-device communication with the first medical device is selected according to an operational mode of a set of operational modes, the operational mode programmed to at least one the first and second medical device,
wherein the set of operational modes includes two or more operational modes,
wherein each operational mode of the set of operational modes indicates a set of chambers in which to deliver pacing pulses using one or both of the first medical device and the second medical device and indicates a set of chambers in which to sense cardiac signals using one or both of the first medical device and the second medical device, and wherein the set of communication protocols comprises two or more communication protocols.

13. The system of claim 12, wherein the first medical device is configured as a leadless atrial pacing device and the second medical device is configured as a leadless ventricular pacing device.

14. The system of claim 12, wherein the first medical device is configured as a leadless right ventricular pacing device and the second medical device is configured as a leadless left ventricular pacing device or wherein the first medical device is configured as a leadless left ventricular pacing device and the second medical device is configured as a leadless right ventricular pacing device.

15. The system of claim 12, further comprising a third medical device configured to be implanted in the patient and to draw power from a non-rechargeable battery housed therein for inter-device communication, and wherein the third medical device is configured as a diagnostic monitor device and each one of the first medical device and the second medical device is configured as a leadless pacing device.

16. The system of claim 12, wherein the second medical device is configured to detect loss of synchronization with the first medical device as the state change of the system and to switch to a resynchronization communication protocol of the set of communication protocols in which power draw from the non-rechargeable battery for inter-device communication with the first medical device is adjusted to a level that is specific to a resynchronization operational mode of the set of operational modes for the first and second medical device to respond to the loss of synchronization and that is less than in magnitude power draw from the rechargeable battery by the first medical device in the resynchronization operational mode for inter-device communication.

17. The system of claim 12, wherein the second medical device is configured to detect a patient arrhythmia as the state change of the system and to switch to a therapy delivery communication protocol of the set of communication protocols in which power draw from the non-rechargeable battery for inter-device communication with the first medical device is adjusted to a level that is specific to a therapy delivery operational mode of the set of operational modes for the first and second medical device to respond to the patient arrhythmia and that is less than in magnitude power draw from the rechargeable battery by the first medical device in the therapy delivery operational mode for inter-device communication.

18. The system of claim 12, wherein the second medical device is configured to detect a request from the first medical device to communicate as the state change of the system and to switch to a data exchange communication protocol of the set of communication protocols in which power draw from the non-rechargeable battery for inter-device communication with the first medical device is adjusted to a level that is specific to a data exchange operational mode of the set of operational modes for the second medical device to respond to the request and that is less than in magnitude power draw from the rechargeable battery by the first medical device in the data exchange operational mode for inter-device communication.

19. The system of claim 12, wherein level of power draw from the non-rechargeable battery by the second device for inter-device communication with the first medical device is less than level of power draw from the rechargeable battery by the first device for inter-device communication with the second medical device for each one of the set of communication protocols that each one of the first and second medical device is configured to execute for inter-device communication.

20. The system of claim 12, wherein level of power draw from the non-rechargeable battery by the second device for inter-device communication with the first medical device is of magnitude to maximize operational lifetime of the non-rechargeable battery.

* * * * *